(12) United States Patent
Yaita

(10) Patent No.: US 9,804,184 B2
(45) Date of Patent: Oct. 31, 2017

(54) AUTOMATED ANALYZER AND METHOD FOR LIFTING AND LOWERING ROD-LIKE MEMBER IN AUTOMATED ANALYZER

(71) Applicant: JEOL Ltd., Tokyo (JP)

(72) Inventor: Tuyoshi Yaita, Tokyo (JP)

(73) Assignee: JEOL Ltd., Tokyo (JP)

( * ) Notice: Subject to any disclaimer, the term of this patent is extended or adjusted under 35 U.S.C. 154(b) by 107 days.

(21) Appl. No.: 14/944,336

(22) Filed: Nov. 18, 2015

(65) Prior Publication Data

US 2016/0187365 A1 Jun. 30, 2016

(30) Foreign Application Priority Data

Nov. 18, 2014 (JP) ................................. 2014-233615

(51) Int. Cl.
| | |
|---|---|
| *G01N 35/10* | (2006.01) |
| *B01F 7/00* | (2006.01) |
| *B01F 7/16* | (2006.01) |
| *G01N 35/00* | (2006.01) |
| *B01L 3/02* | (2006.01) |

(52) U.S. Cl.
CPC ...... *G01N 35/1011* (2013.01); *B01F 7/00258* (2013.01); *B01F 7/161* (2013.01); *B01L 3/0293* (2013.01); *G01N 35/00584* (2013.01); *G01N 35/1002* (2013.01); *G01N 35/1004* (2013.01); *B01L 2200/0615* (2013.01); *B01L 2200/141* (2013.01); *B01L 2300/0838* (2013.01); *G01N 2035/00534* (2013.01)

(58) Field of Classification Search
CPC ........... G01N 35/1011; G01N 35/1004; G01N 35/00584; G01N 35/1002; G01N 2035/00534; B01L 3/0293; B01L 2200/141; B01L 2200/0615; B01L 2300/0838; B01F 7/00258; B01F 7/161
See application file for complete search history.

(56) References Cited

U.S. PATENT DOCUMENTS

| | | | |
|---|---|---|---|
| 7,955,865 B2 * | 6/2011 | Marziali | B01J 19/0046 422/501 |
| 8,852,530 B2 | 10/2014 | Oonuma et al. | |
| 2010/0210007 A1 * | 8/2010 | Iwamura | G01N 35/1011 435/286.2 |
| 2013/0259745 A1 * | 10/2013 | Yamazaki | G01N 35/1009 422/63 |

FOREIGN PATENT DOCUMENTS

| | | |
|---|---|---|
| CN | 102192997 A | 9/2011 |
| JP | 9184846 A | 7/1997 |
| JP | 2010271203 A | 12/2010 |

* cited by examiner

*Primary Examiner* — Lore Jarrett
(74) *Attorney, Agent, or Firm* — The Webb Law Firm

(57) ABSTRACT

An automated analyzer includes a rod-like member 12a, a driving portion 12c, and a control mechanism 30. The driving portion 12c lifts and lowers the rod-like member 12a a direction of being inserted into and removed from the container 24. The control mechanism 30 controls the driving portion 12c so that the rod-like member 12a is lifted after being lowered so that a tip portion of the rod-like member 12a reaches a first position in the liquid L, and at a time when the rod-like member 12a reaches a second position where the tip portion is not separated from the liquid, an upward motion of the rod-like member 12a is stopped for a given period of time to reduce liquid film adhering to the rod-like member.

7 Claims, 9 Drawing Sheets

| PARAMETER | HIGH (DEEP) | MEDIUM (MEDIUM POSITION) | LOW (SHALLOW) |
|---|---|---|---|
| a (VISCOSITY) | 2 | 1 | 0 |
| b (SURFACE TENSION) | 0 | 1 | 2 |
| c (FIRST POSITION) | 2 | 1 | 0 |

(C)

(D)

(E)

(A)

(B)

AUTOMATED ANALYZER AND METHOD FOR LIFTING AND LOWERING ROD-LIKE MEMBER IN AUTOMATED ANALYZER

BACKGROUND OF THE INVENTION

Field of the Invention

The present invention relates to an automated analyzer and a method for lifting and lowering a rod-like member in the automated analyzer. Particularly, the present invention relates to a method for lifting and lowering a stirring bar that performs stirring, or a rod-like member such as a probe that performs injection/suction.

Description of the Related Art

For example, a biochemical analyzer for analyzing various components contained in a specimen such as blood or urine is known as the automated analyzer. In the biochemical analyzer, a reagent corresponding to an item of analysis and a specimen are mixed and caused to react with each other within a reaction container. In addition, the biochemical analyzer analyzes a specific component of the specimen by irradiating the specimen reacting with a reagent, with light and using the photometry results.

Such a biochemical analyzer includes a dispensing mechanism in which a liquid such as a specimen or a reagent is dispensed between two containers, and a stirring mechanism in which a mixed liquid of the dispensed regent and specimen is uniformly stirred. The dispensing mechanism includes a probe for dispensing a liquid. The stirring mechanism includes a stirring bar that uniformly stirs the mixed liquid. Furthermore, the biochemical analyzer includes a cleaning mechanism for cleaning a liquid such as the specimen or reagent which adheres to a tip portion of the rod-like member such as the probe or stirring bar.

At the dispensing operation, first, a probe of the dispensing mechanism moves down to a liquid surface of a reagent which is stored in a reagent container, and after a tip of the probe reaches a desired depth under the liquid surface of the reagent, a suction operation of the reagent by the probe is conducted. Next, while holding the sucked reagent in the probe, there is performed an operation of moving the probe from the reagent container to the targeted reaction container. In addition, the reagent in the probe is discharged into a reaction solution which is stored in the reaction container.

Incidentally, during the above dispensing procedures, excessive liquid droplets adhere to the tip portion of the probe since the probe lifts and lowers relative to the container and the tip of the probe makes contact with the specimen, reagent or cleaning liquid. In addition, when the excessive liquid droplets are admixed to, for example, the reaction container, there is unevenness in the absolute amount of the dispensed liquid. Furthermore, during the cleaning procedure, when the cleaning liquid adhering to the tip of the probe is admixed to, for example, a reagent container or the reaction container, the reagent or the reaction solution is diluted. Thereby, accuracy in analysis of the automated analyzer is lowered. In addition, during the movement of the probe, contamination of machinery is also generated due to scattering the excessive liquid droplets.

As a countermeasure for reducing such liquid droplets adhering to the tip portion of the rod-like member, Japanese Patent Laid-Open Publication No. 09-184846 proposes a liquid sample dispensing device having a small amount discharging means that discharges a small amount of liquid and a nozzle moving mechanism that lifts and lowers nozzles. Specifically, the liquid droplets adhering to the nozzle are removed by rapidly accelerating and rapidly decelerating the nozzles when lifting and lowering the nozzles by the nozzle moving mechanism.

Furthermore, in Japanese Patent Laid-Open Publication No. 2010-271203, there is proposed a sampling method which has a step of moving a dispensing nozzle up at a given rate, and a step of moving the dispensing nozzle up at a rate larger than the given rate after detecting removal of the dispensing nozzle from the sample. Specifically, the liquid droplets adhering to the nozzle are reduced by changing the pattern of the upward motion of the nozzle before and after the removal of the nozzle tip portion from the liquid.

DISCLOSURE OF THE INVENTION

Problems to be Solved by the Invention

However, by the technique described in Japanese Patent Laid-Open Publication No. 09-184846, there is a problem in which a liquid in the probe which is necessary for dispensing is also discharged from the probe together with the excessive liquid droplets, by lifting and lowering the nozzle correspond to the probe. Therefore, the accuracy of the automated analyzer has been lowered according to the technique described in Japanese Patent Laid-Open Publication No. 09-184846.

Furthermore, when the probe tip portion starts the upward motion from the contact state with the liquid, a thin liquid film adheres to the surface of the probe due to a friction force and surface tension which are generated on the contact surface of the liquid and the probe. In addition, when the probe continues the upward motion, there is reached a condition in which the friction force acts between the liquid and the probe. Therefore, when the probe tip portion is removed from the liquid surface, the liquid that follows the surface of the probe adheres to the probe tip portion in liquid droplets. In the technique of Japanese Patent Laid-Open Publication No. 2010-271203, although the moving speed of the dispensing nozzle corresponding to the probe is set to a low rate, the probe is pulled out at a constant rate from the liquid surface. Therefore, it cannot be said that the technique described in Japanese Patent Laid-Open Publication No. 2010-271203 has enough effect of reducing the liquid droplets adhering to the probe tip portion.

Accordingly, an object of the present invention is to provide an automated analyzer which reduces the liquid droplets adhering to the tip portion of the rod-like member and which gives a high accuracy, and a method for lifting and lowering a rod-like member in the automated analyzer.

SUMMARY OF THE INVENTION

Means for Solving the Problem

In order to solve the above problem, the automated analyzer of the present invention has a rod-like member inserted into and removed from a container where a liquid is stored, a driving portion, and a control mechanism. The driving portion lifts and lowers the rod-like member in the direction of being inserted into and removed from the container. The control mechanism controls the driving portion so that the rod-like member is lifted after being lowered so that a tip portion of the rod-like member reaches a first position in the liquid, and at a time when at least the rod-like member reaches a second position where the tip portion is not separated from the liquid, an upward motion of the rod-like member is stopped for a given period of time, and then, after elapsing the given period of time, the rod-like member is lifted to a position where the tip portion is separated from the liquid.

Furthermore, the method for lifting and lowering a rod-like member in the automated analyzer of the present invention has the following first step to the third step. In the first step, the rod-like member is lowered in the direction where a tip portion of the rod-like member makes contact with a liquid which is stored in a container, and reaches a first position in the liquid. In the second step, after completing the first step, the rod-like member is lifted, and at a time when at least the rod-like member reaches a second position where the tip portion is not separated from the liquid, the upward motion of the rod-like member is stopped for a given period of time. In the third step, after completing the second step, the rod-like member is lifted to a position where the tip portion is separated from the liquid.

Effects of the Invention

As explained above, according to the present invention, it is possible to reduce the liquid droplets adhering to the tip portion of the rod-like member and to obtain high analytical accuracy.

BRIEF DESCRIPTION OF THE DRAWINGS

FIGS. 5(A) and 5(B) are explanatory views showing the flow of a method for lifting and lowering a probe according to the first embodiment of the present invention.

DESCRIPTION OF THE PREFERRED EMBODIMENTS

Figure 1:
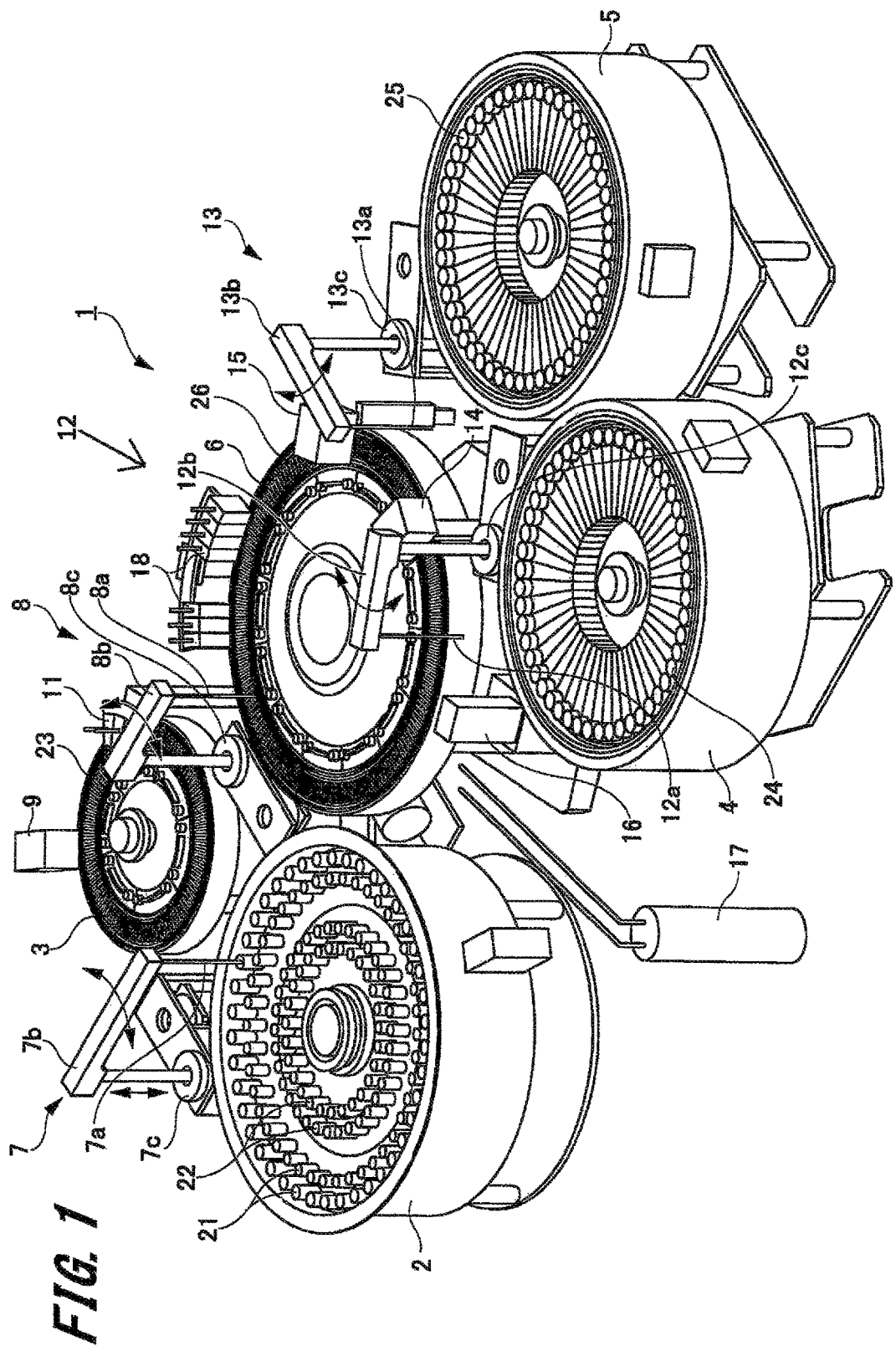
FIG. 1 is a perspective view of the configuration of an automated analyzer according to a first embodiment of the present invention.

Hereinafter, the preferred embodiments of the automated analyzer and the method for lifting and lowering the rod-like member in the automated analyzer of the present invention will be described with reference to FIGS. 1 to 12. Note that the same reference numerals are attached to common members. In addition, the explanation will be given in the following order, but the present invention is not limited to the following embodiments.

1. First exemplary embodiment
   1-1. Configuration of automated analyzer
   1-2. Configuration of control mechanism in the automated analyzer
   1-3. Method for operating the probe up and down in the automated analyzer
2. Second exemplary embodiment
   2-1. Configuration of automated analyzer
   2-2. Method for operating stirring mechanism in automated analyzer 1. First Exemplary Embodiment 1-1. Configuration of Automated Analyzer First, a first exemplary embodiment of the automated analyzer of the present invention (hereinafter, referred to as "the present exemplary embodiment") will be described by referring to FIG. 1.

FIG. 1 is a perspective schematic view of the automated analyzer of the present exemplary embodiment.

The device shown in FIG. 1 is a biochemical analyzer applied as one example of the automated analyzer 1 of the present invention. The biochemical analyzer is a device for automatedally measuring the amount of a certain component contained in a biological sample such as blood or urine.

As shown in FIG. 1, the automated analyzer 1 includes a sample turntable 2, a dilution turntable 3, a first reagent turntable 4, a second reagent turntable 5, and a reaction turntable 6. In addition, the automated analyzer 1 includes a sample diluting dispensing mechanism 7, a sampling dispensing mechanism 8, a dilution and stirring mechanism 9, a dilution cleaner 11, a first reagent dispensing mechanism 12, a second reagent dispensing mechanism 13, a first reaction stirring mechanism 14, a second reaction stirring mechanism 15, a multi-wavelength photometer 16, a thermostatic bath 17, and reaction container cleaner 18. Furthermore, the automated analyzer 1 includes a control mechanism 30 described below (refer to FIG. 2).

The sample turntable 2 is so formed in the form of a container that is substantially cylindrical and is open at one end in the axial direction. A plurality of specimen containers 21 and a plurality of dilution liquid containers 22 are stored in the sample turntable 2. A specimen (sample) including blood, urine, or the like is stored in each specimen container 21. A special dilution liquid other than physiological salt solution that is a normal dilution liquid is stored in each of the dilution liquid containers 22.

The plurality of specimen containers 21 is arranged at predetermined intervals in the circumferential direction of the sample turntable 2. In addition, two rows of the specimen containers 21 arranged in the circumferential direction of the sample turntable 2 are set at predetermined intervals in the radial direction of the sample turntable 2.

The plurality of dilution liquid containers 22 is arranged inside the rows of the specimen containers 21, in the radial direction of the sample turntable 2. The plurality of dilution liquid containers 22 is arranged side by side at predetermined intervals in the circumferential direction of the sample turntable 2 in the same way as the specimen containers 21. In addition, two rows of the dilution liquid containers 22 arranged in the circumferential direction of the sample turntable 2 are set at predetermined intervals in the radial direction of the sample turntable 2.

Note that the arrangement of the plurality of specimen containers 21 and the plurality of dilution liquid containers 22 is not limited to two rows. The arrangement may be one row, or may be three or more rows in the radial direction of the sample turntable 2.

The sample turntable 2 is supported by a driving mechanism (not shown) so as to be rotatable along the circumferential direction. In addition, the sample turntable 2 is rotated in the circumferential direction at a given speed by each given angular range by the driving mechanism (not shown). Additionally, the dilution turntable 3 is arranged around the sample turntable 2.

Each of the dilution turntable 3, first reagent turntable 4, second reagent turntable 5, and reaction turntable 6 is so formed to be a container that is in a substantially cylindrical shape and that is open at one end in the axial direction in the same way as the sample turntable 2. The dilution turntable 3, first reagent turntable 4, second reagent turntable 5, and reaction turntable 6 are rotated in the circumferential direction at a given speed by each given angular range by the driving mechanism (not shown). Note that the reaction turntable 6 is set so as to make more than a half revolution at one time of the movement.

A plurality of dilution containers 23 is arranged in the circumferential direction of the dilution turntable 3 and is stored in the dilution turntable 3. Specimens which are sucked from the specimen containers 21 arranged in the sample turntable 2, and are diluted (hereinafter referred to as "diluted specimen"), are stored in the dilution containers 23.

A plurality of first reagent containers 24 is arranged in the circumferential direction of the first reagent turntable 4 and stored in the first reagent turntable 4. In addition, a plurality of second reagent containers 25 is arranged in the circumferential direction of the second reagent turntable 5 and is stored in the second reagent turntable 5. Additionally, a condensed first reagent is stored in the first reagent containers 24. A condensed second reagent is stored in the second reagent containers 25. Note that, in the first reagent container 24 or the second reagent container 25, there is a case where a non-condensed first reagent or a non-condensed second reagent is stored.

Furthermore, the first reagent turntable 4, first reagent containers 24, second reagent turntable 5, and second reagent container 25 are kept at a given temperature by a cold storage mechanism (not shown). Therefore, the first reagent stored in the first reagent containers 24 and the second reagent stored in the second reagent containers 25 are cold-insulated at the given temperature.

The reaction turntable 6 is arranged among the dilution turntable 3, first reagent turntable 4, and second reagent turntable 5. A plurality of reaction containers 26 is arranged in the circumferential direction of the reaction turntable 6 and is stored in the reaction turntable 6. A diluted specimen sampled from any of the dilution containers 23 in the dilution turntable 3, the first reagent sampled from any of the first reagent containers 24 in the first reagent turntable 4, and the second reagent sampled from any of the second reagent containers 25 in the second reagent turntable 5 are injected into the reaction containers 26. In addition, in each of these reaction containers 26, the diluted specimen, first reagent, and second reagent are stirred together and are caused to react with each other.

The sample diluting dispensing mechanism 7 is arranged around the sample turntable 2 and around the dilution turntable 3. Additionally, the sample diluting dispensing mechanism 7 includes a probe 7a which is one example of the rod-like member, an arm 7b to which the probe 7a is attached, and a driving portion 7c which movably supports the arm 7b.

The probe 7a is movably supported by the driving portion 7c via the arm 7b in the axial direction of the sample turntable 2 and of the dilution turntable 3 (for example, in the vertical direction). Furthermore, the probe 7a is rotatably supported by the driving portion 7c via the arm 7b, along the horizontal direction that is substantially parallel to the openings of the sample turntable 2 and dilution turntable 3. In addition, the probe 7a reciprocates between the sample turntable 2 and the dilution turntable 3 by rotating along the horizontal direction. Note that, when the probe 7a moves between the sample turntable 2 and the dilution turntable 3, the probe 7a passes through a cleaner (not shown).

Here, the operation of the sample diluting dispensing mechanism 7 will be described.

When the probe 7a has moved into a given position located above the opening of the sample turntable 2, the driving portion 7c lowers the arm 7b in the axial direction of the sample turntable 2, and the probe 7a formed on the tip portion thereof is inserted into the specimen containers 21. At this time, a sampling pump (not shown) is operated such that the probe 7a sucks in a given amount of the specimen from the specimen container 21. Then, the driving portion 7c lifts the arm 7b in the axial direction of the sample turntable 2 and pulls the probe 7a out of the specimen container 21. In addition, the driving portion 7c rotates the probe 7a via the arm 7b in the horizontal direction and move the probe 7a into a given position located above the opening of the dilution turntable 3.

Next, the driving portion 7c lowers the arm 7b in the axial direction of the dilution turntable 3 and inserts the probe 7a into a given dilution container 23. In addition, the probe 7a discharges the sucked specimen into the dilution container 23. Then, the probe 7a is cleaned by the cleaner.

The sampling dispensing mechanism 8 is arranged between the dilution turntable 3 and the reaction turntable 6. Furthermore, the sampling dispensing mechanism 8 includes a probe 8a which is one example of the rod-like member, an arm 8b to which the probe 8a is attached, and a driving portion 8c which movably supports the arm 8b.

The probe 8a is supported by the driving portion 8c via the arm 8b so as to be movable and rotatable in the axial direction (vertical direction) and in the horizontal direction of the dilution turntable 3, in the same way as the probe 7a of the sample diluting dispensing mechanism 7. In addition, the probe 8a reciprocates between the dilution turntable 3 and the reaction turntable 6.

The sampling dispensing mechanism 8 inserts the probe 8a into the dilution containers 23 in the dilution turntable 3 by the driving portion 8c via the arm 8b and sucks a given amount of diluted specimen. Then, the sampling dispensing mechanism 8 discharges the sucked diluted specimen into the reaction container 26 in the reaction turntable 6.

The first reagent dispensing mechanism 12 is arranged between the reaction turntable 6 and the first reagent turntable 4, and the second reagent dispensing mechanism 13 is arranged between the reaction turntable 6 and the second reagent turntable 5. The first reagent dispensing mechanism 12 includes a probe 12a which shows one example of the rod-like member of the present exemplary embodiment, an arm 12b to which the probe 12a is attached, and a driving portion 12c which movably supports the arm 12b.

The probe 12a is supported by the driving portion 12c via the arm 12b so as to be movable in the axial direction (vertical direction) and movable in the horizontal direction of the reaction turntable 6 and rotatable, in the same way as the probe 7a of the sample diluting dispensing mechanism 7. Then, the probe 12a reciprocates between the first reagent turntable 4 and the reaction turntable 6.

The first reagent dispensing mechanism 12 inserts the probe 12a into the first reagent containers 24 in the first reagent turntable 4 by the driving portion 12c via the arm 12b and sucks a given amount of the first reagent. Then, the first reagent dispensing mechanism 12 discharges the sucked first reagent into the reaction container 26 in the reaction turntable 6. In addition, the detailed lifting and lowering motion of the probe 12a in the first reagent dispensing mechanism 12 will be described later.

Furthermore, the second reagent dispensing mechanism 13 includes a probe 13a which shows one example of the rod-like member, an arm 13b to which the probe 13a is attached, and a driving portion 13c which movably supports the arm 13b.

The probe 13a is supported by the driving portion 13c via the arm 13b so as to be movable in the axial direction (vertical direction) and movable in the horizontal direction of the reaction turntable 6 and rotatable, in the same way as the probe 7a of the sample diluting dispensing mechanism 7. Then, the probe 13a reciprocates between the second reagent turntable 5 and the reaction turntable 6.

The second reagent dispensing mechanism 13 inserts the probe 13a into the second reagent containers 25 in the second reagent turntable 5 by the driving portion 13c via the arm 13b and sucks a given amount of the second reagent. Then, the second reagent dispensing mechanism 13 discharges the sucked second reagent into the reaction container 26 in the reaction turntable 6.

The dilution and stirring mechanism 9 and the dilution cleaner 11 are arranged around the dilution turntable 3. The dilution and stirring mechanism 9 inserts a stirring bar which shows one example of the rod-like member (not shown) into the dilution containers 23 and stirs together the specimen and the dilution liquid.

The dilution cleaner 11 is a device that cleans the dilution container 23 after the diluted specimen has been sucked by the sampling dispensing mechanism 8. The dilution cleaner 11 has a plurality of nozzles for cleaning dilution containers. The plurality of dilution container cleaning nozzles is connected to a waste liquid pump not shown and with a detergent pump not shown. The dilution cleaner 11 inserts the dilution container cleaning nozzles into the dilution containers 23, and drives the waste liquid pump to thereby suck the diluted specimens remaining in the dilution containers 23 by the inserted dilution container cleaning nozzles. Then, the dilution cleaner 11 discharges the sucked diluted specimens into the waste liquid tank not shown.

Subsequently, the dilution cleaner 11 supplies a detergent into the dilution container cleaning nozzles from the detergent pump, and discharges the detergent into the dilution containers 23 from the dilution container cleaning nozzles. The inside of each of the dilution containers 23 is cleaned with the detergent. After that, the dilution cleaner 11 sucks the detergent by the dilution container cleaning nozzles and dries the inside of each of the dilution containers 23.

The first reaction stirring mechanism 14, the second reaction stirring mechanism 15, and the reaction container cleaners 18 are arranged around the reaction turntable 6. The first reaction stirring mechanism 14 inserts a stirring bar which shows one example of the rod-like member (not shown) into the reaction containers 26 and stirs together the diluted specimen and the first reagent. Consequently, a reaction between the diluted specimen and the first reagent is uniformly and quickly carried out. Since the configuration of the first reaction stirring mechanism 14 is identical to that of the dilution and stirring mechanism 9, an explanation thereof is omitted here.

The second reaction stirring mechanism 15 inserts the stirring bar which shows one example of the rod-like member (not shown) into the reaction containers 26 and stirs together the diluted specimen, first reagent, and second reagent. Thereby, a reaction between the diluted specimen, first reagent, and second reagent is uniformly and quickly carried out. Since the configuration of the second reaction stirring mechanism 15 is identical to that of the dilution and stirring mechanism 9, an explanation thereof is omitted here.

Each of the reaction container cleaners 18 is a device for cleaning the inside of the reaction container 26 having completed an inspection. The reaction cleaner 18 has a plurality of reaction container cleaning nozzles. The plurality of reaction container cleaning nozzles is connected to the waste liquid pump (not shown) and to the detergent pump (not shown), in the same way as the dilution container cleaning nozzles. Note that a cleaning process by the reaction container cleaner 18 is the same as that by above-described dilution cleaner 11, and thus description thereof is omitted.

Furthermore, the multi-wavelength photometer 16 is arranged to face the outer peripheral wall of the reaction turntable 6 around the reaction turntable 6. The multi-wavelength photometer 16 is inserted into the reaction containers 26, performs optical measurements on the diluted specimen having reacted with the first and second reagents, outputs the amounts of various components of the specimen in terms of numerical data known as "absorbance", and detects a reaction state of the diluted specimen.

Moreover, the thermostatic bath 17 is arranged around the reaction turntable 6. The thermostatic bath 17 is configured to keep constant the temperature of the reaction containers 26 arranged in the reaction turntable 6 at all times.

Note that the driving method of each of the elements of the automated analyzer 1 described above is controlled by the following control mechanism 30. Meanwhile, each member means the sample turntable 2, the dilution turntable 3, the first reagent turntable 4, the second reagent turntable 5, and the reaction turntable 6. In addition, each member means the sample diluting dispensing mechanism 7, the sampling dispensing mechanism 8, the dilution and stirring mechanism 9, the dilution cleaner 11, the first reagent dispensing mechanism 12, the second reagent dispensing mechanism 13, the first reaction stirring mechanism 14, the second reaction stirring mechanism 15, the multi-wavelength photometer 16, the thermostatic bath 17, and the reaction container cleaner 18.

1-2. Configuration of Control Mechanism in Automated Analyzer

Next, the detailed configuration of the control mechanism 30 will be explained using FIG. 2.

Figure 2:
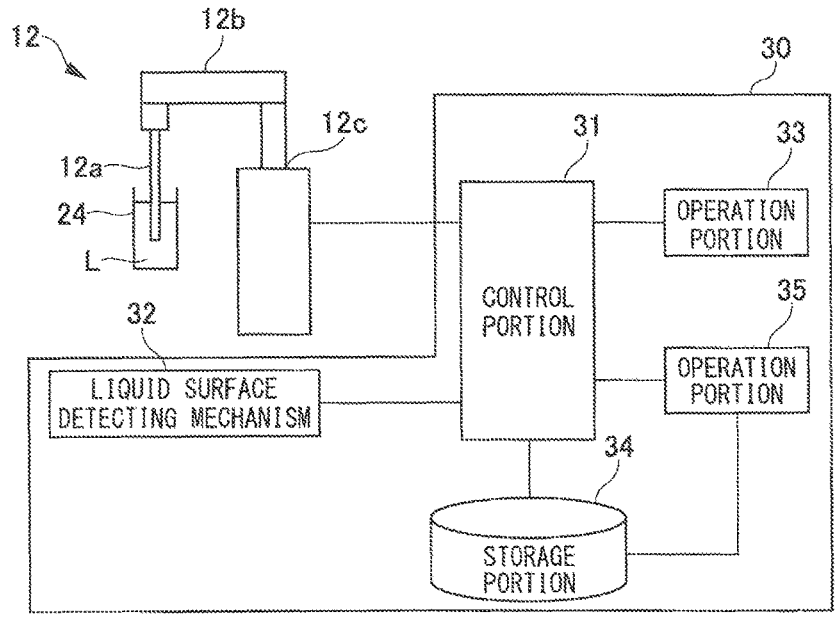
FIG. 2 is a block diagram showing the control mechanism, in the automated analyzer according to the first embodiment of the present invention.

FIG. 2 is a block chart showing the control mechanism, in the automated analyzer according to the exemplary embodiment. Here, as one example, the control mechanism 30 controls the drive of the first reagent dispensing mechanism (hereinafter, referred to as "reagent dispensing mechanism") 12. Furthermore, hereinafter, "first reagent" is simply described as "reagent", the "first reagent container 24" is simply described as "reagent container 24", and the "first reagent turntable 4" is simply described as "reagent turntable 4".

As shown in FIG. 2, the control mechanism 30 includes a control portion 31, a liquid surface detecting mechanism 32, an operation portion 33, a storage portion 34, and a calculation portion 35. In addition, the control mechanism 30 is connected to the driving portion 12c of the reagent dispensing mechanism 12. Additionally, the control mechanism 30 controls the lifting and lowering motion of the probe 12a via the arm 12b by controlling the driving portion 12c of the reagent dispensing mechanism 12.

[Control Portion 31]

The control portion 31 is constituted of a CPU (Central Processing Unit), and the like. In addition, the control portion 31 is connected to the reagent dispensing mechanism 12, the liquid surface detecting mechanism 32, the operation portion 33, the storage portion 34, and the calculation portion 35. Furthermore, the control portion 31 controls the reagent dispensing mechanism 12, the liquid surface detecting mechanism 32, the operation portion 33, the storage portion 34, and the calculation portion 35.

Specifically, the control portion 31 controls a motion amount and motion speed in the lifting and lowering motion, the rotation direction, rotation angle and rotation rate in the rotation motion of the reagent dispensing mechanism 12, and the suction or discharging operation and cleaning operation of the probe 12a.

[Liquid Surface Detecting Mechanism 32]

The liquid surface detecting mechanism 32 is arranged near each of the reaction turntable 6 and the reagent turntable 4 (refer to FIG. 1). The liquid surface detecting mechanism 32 detects, for example, the position of the liquid surface of the reagent L stored in the reagent container 24 under controlling by the control portion 31.

For example, an electrostatic capacitance system that utilizes a change of electrostatic capacitance is used as the liquid surface detecting mechanism 32. According to the electrostatic capacitance system, a minute change of the electrostatic capacitance between the probe 12a and the reagent L stored in the reagent container 24 is measured by a sensor or the like. Next, the liquid surface is detected by utilizing a change of the electrostatic capacitance when the tip portion of the probe 12a contacts with the liquid surface of the reagent L. The information on the detected liquid surface (hereinafter, referred to as "liquid surface detecting information") is sent to the storage portion 34 by the liquid surface detecting mechanism 32. The storage portion 34 receives the liquid surface detecting information, and stores and keeps the information.

Note that the liquid surface detecting mechanism 32 is not limited to the electrostatic capacitance system, and may be, for example, a system that detects a pressure in a piping (not shown) which is connected with the probe 12a, or may be an optical system.

[Operation Portion 33]

The operation portion 33 is configured to be selectively operated by a touch panel operation or a cursor operation. Furthermore, the operation portion 33 includes a display portion 33a (refer to FIG. 3). The display portion 33a displays a setting screen which accepts the operating input by users.

Figure 3:
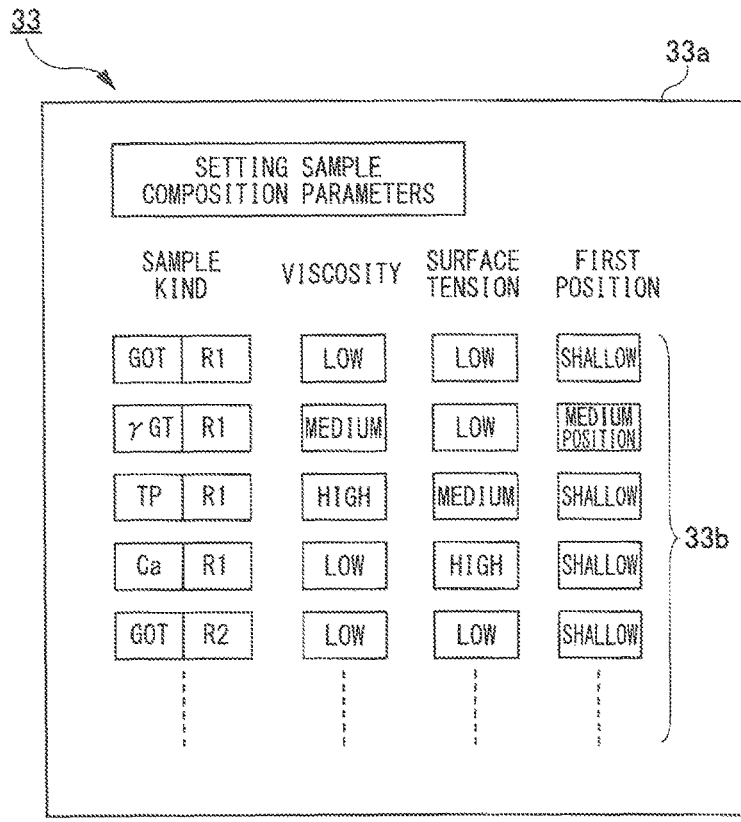
FIG. 3 is a view showing one example of the setting screen which is displayed on a display portion in an operation portion of a control mechanism, shown in FIG. 2.

FIG. 3 shows one example of the setting screen displayed on the display portion 33a in the operation portion 33.

Here, there is shown a screen for setting information to be used in calculating the stop time of the probe 12a described below (hereinafter, referred to as "calculation information") is displayed as one example. In the display portion 33a, there is displayed a plurality of setting portions 33b so as to be able to selectively operate the calculation information of the "viscosity", "surface tension" and "first position" corresponding to a plurality of "types of samples". In addition, the operation portion 33 sends the selectively operated information to the storage portion 34. The storage portion 34 receives the selectively operated information, and stores and keeps the information.

A type of the reagent L stored in the reagent container 24 is displayed in the left line of the "Types of samples". For example, the uppermost "GOT" indicates a reagent used for measuring GOT isozyme (m-GOT) in a plasma and serum. Furthermore, a type of the reagent turntables storing the reagent containers 24 is displayed in the right line of the "Types of samples". For example, the uppermost "R1" indicates the "first reagent turntable 4".

The "viscosity" and "surface tension" mean the composition of the reagent L stored in the reagent container 24. In addition, in the "viscosity" and "surface tension", the setting portions 33b of three stages: "high", "medium", and "low" are set.

The "first position" is a position of the tip portion of the probe 12a at the time when the downward motion of the probe 12a is completed (refer to FIG. 5B), in the lifting and lowering motion described below. Furthermore, the "first position" is a position where the reagent L in the reagent container 24 is sucked by the probe 12a. In addition, the setting portions 33b of three stages: "deep", "medium position", and "shallow" are set as to the "first position".

Note that the first position P1 may be set, for example, for every reagent container 24 stored in the reagent turntable 4, or for every type of the stored reagent L. Furthermore, the first position P1 may be set depending on a size or shape of the reagent container 24, or an amount of the liquid of the reagent L which is stored in the reagent container 24. For example, in the case where the reagent L in the reagent container 24 is easily shaken due to the shape of the reagent container 24, the first position P1 is set to a deep position from the liquid surface S.

[Storage Portion 34]

The storage portion 34 is constituted of a storage device with a large capacitance such as HDD (Hard disk drive). In addition, the storage portion 34 is connected not only to the control portion 31 but also to the calculation portion 35. Additionally, the storage portion 34 sends the information to and receives from the liquid surface detecting mechanism 32, the operation portion 33, the storage portion 34 and the calculation portion 35 of the control mechanism 30 under control by the control portion 31. In the storage portion 34, there are stored and held a program, information and a table of parameter, for conducting the dispensing operation.

Examples of the program include a control program for controlling the motion of the reagent dispensing mechanism 12, a calculation program for calculating the amount of the upward motion of the probe 12a or the stop time of the probe 12a, and the like. Examples of the "information" include the liquid surface detecting information, the calculation information, the information calculated in the calculation portion 35, and the like.

The table of the parameter (hereinafter, referred to as "parameter table") is a value of each parameter which is set corresponding to the calculation information stored and held in the storage portion 34.

Figures 4, 5:
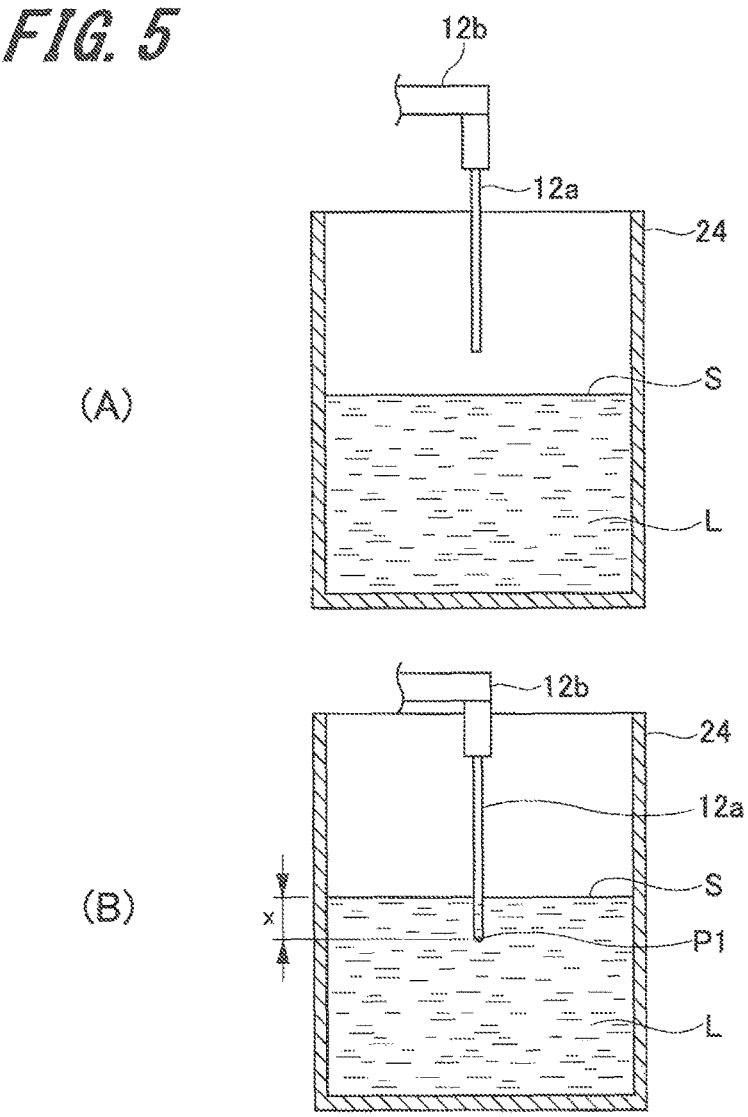
FIG. 4 is a view showing one example of a parameter table which is installed in a storage portion of the control mechanism, shown in FIG. 2.

FIG. 4 is a view showing one example of the parameter table which is used in calculating the stop time of the probe 12a described below.

In the parameter table shown in FIG. 4, there are shown, as the calculation information, the "viscosity", the "surface tension", and the "first position" which are displayed in the display portion 33a shown in FIG. 3. The "viscosity" of the calculation information is represented by a parameter a, the "surface tension" is represented by a parameter b, and the "first position" is represented by a parameter c. Furthermore, in the parameter table, respective values are set corresponding to the setting portion 33b of the "high (deep)", "medium (medium position)", and the "low (shallow)" displayed on the display portion 33a shown in FIG. 3.

For example, in the "viscosity", a value of the parameter a is "2" in the case where the "high" is set, a value of the parameter a is "1" in the case where the "medium" is set, and a value of the parameter a is "0" in the case where the "low" is set. In addition, in the "surface tension", a value of the parameter b is "0" in the case where the "high" is set, a value of the parameter b is "1" in e case where the "medium" is set, and a value of the parameter b is "2" in the case where the "low" is set. Additionally, in the "first position", a value of the parameter c is "2" in the case where the "deep" is set, a value of the parameter c is "1" in the case where the "medium position" is set, and a value of the parameter c is "0" in the case where the "shallow" is set. Note that the value of each parameter is not limited to the value shown in the drawing, and is appropriately set in accordance with the purpose and the intended use.

[Calculation Portion 35].

The calculation portion 35 is constituted of, for example, a CPU (Central Processing Unit), or the like. In addition, the calculation portion 35 conducts calculation processing based on the program and calculation information obtained from the storage portion 34. Such a calculation portion 35 calculates the amount of the upward motion of the probe 12a or the stop time.

1-3. Method for Lifting and Lowering Probe in Automated Analyzer

Next, the method for lifting and lowering the probe in the automated analyzer 1 will be explained using FIGS. 3 to 8.

Figure 6:
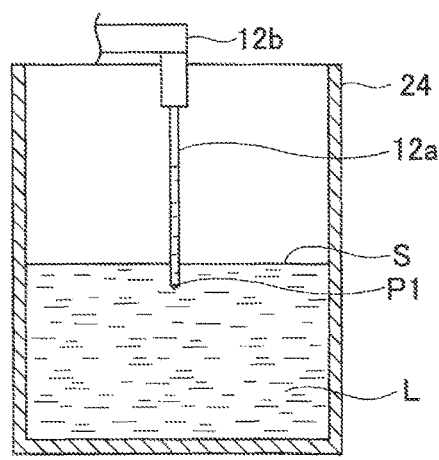
FIGS. 6(C) to 6(E) are explanatory views showing the flow of the method for lifting and lowering the probe according to the first embodiment of the present invention.
Figure 6:
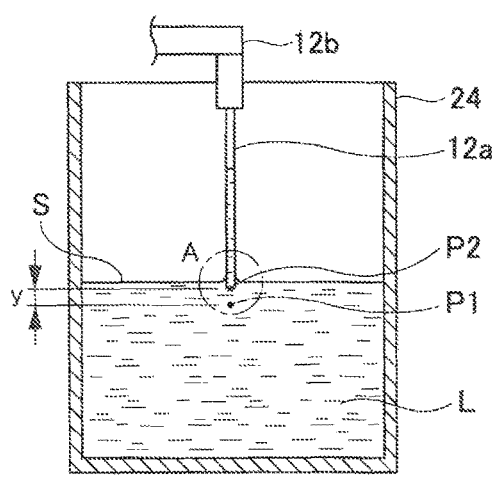
Figure 6:
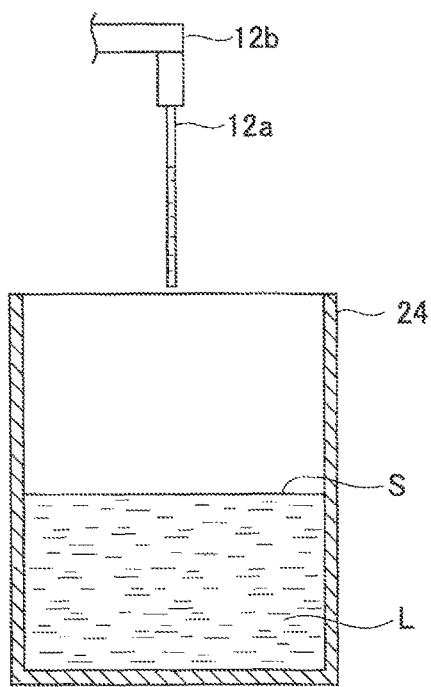
Figure 7:
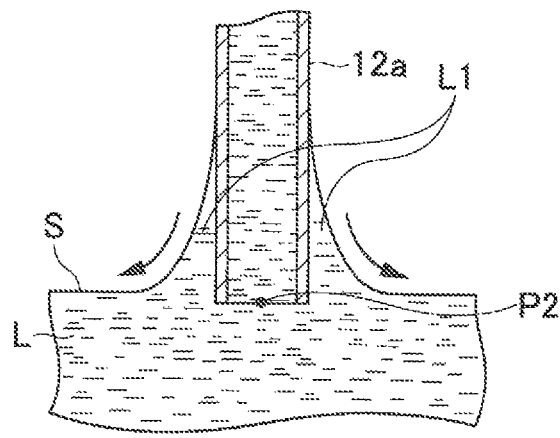
FIGS. 7(A) and 7(B) are enlarged views of the tip portions of the probes shown in FIG. 6(D).
Figure 7:
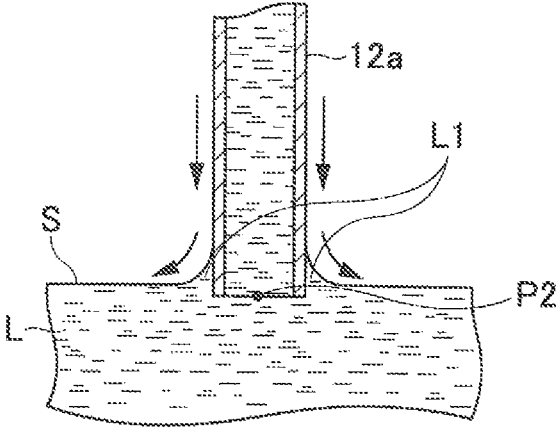
Figure 8:
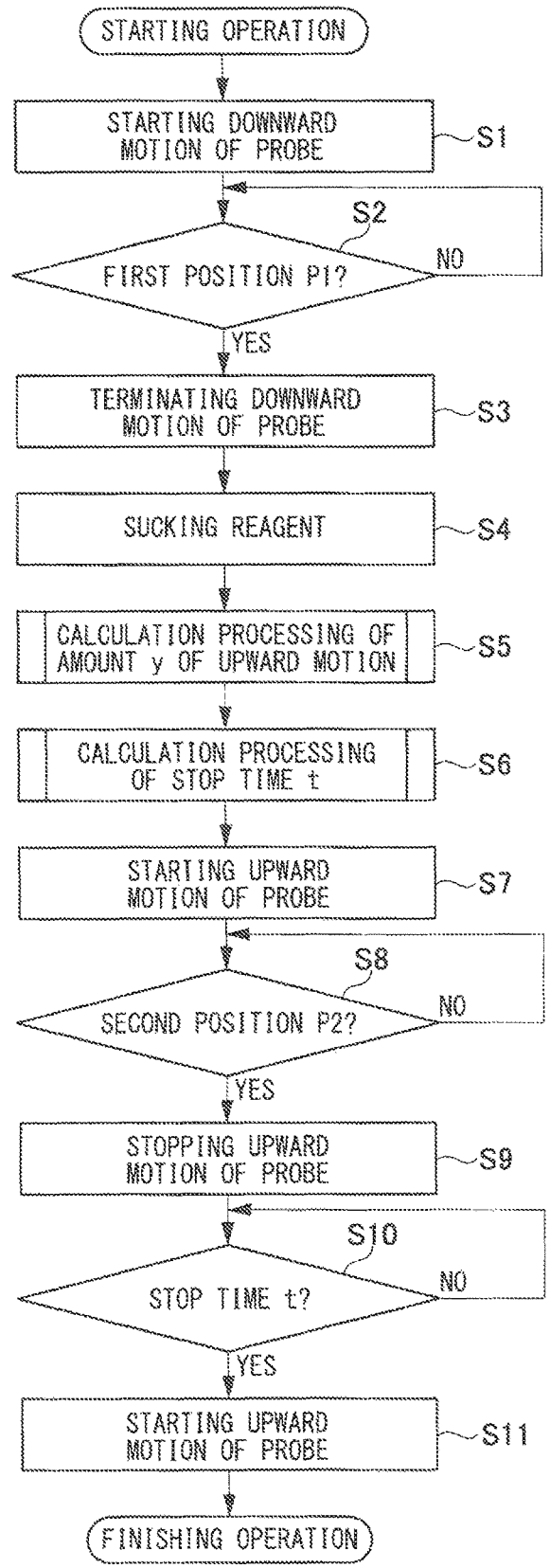
FIG. 8 is a flow chart showing the method for lifting and lowering the probe in the automated analyzer according to the first embodiment of the present invention.

FIGS. 5 to 6 are explanatory views showing the flow of the method for lifting and lowering the probe in the automated analyzer of the present exemplary embodiment. FIG. 7 is an enlarged view of the tip portion of the probes shown in FIG. 6(D). FIG. 8 is a flow chart showing the method for lifting and lowering the probe in the automated analyzer of the present exemplary embodiment.

Note that, here, there will be explained, as one example, a suction operation at the time of the dispensing by the reagent dispensing mechanism 12. Namely, explanation will be given by taking as an example the case where, as the motion of the reagent dispensing mechanism 12, the probe 12a is moved down to the reagent container 24, a given amount of the reagent L in the reagent container 24 is sucked from the tip portion of the probe 12a, and then the probe 12a is lifted.

Furthermore, the following procedures are started, as shown in FIG. 5A, at the time when the reagent container 24 to be sucked among a plurality of reagent containers 24 stored in the reagent turntable 4 reaches the dispensing position. The reagent container 24 to be sucked moves to the dispensing position by rotationally driving the reagent turntable 4. The reagent turntable 4 is rotationally driven by the fact that the control mechanism 30 controls the drive of a driving mechanism (not shown). Note that the user inputs, in the operation portion 33 shown in FIG. 3, the viscosity and surface tension of the reagent L to be dispensed, and the first position of the reagent container 24 to be dispensed.

First, the control portion 31 acquires the set first position P1 from the storage portion 34. Then, the control portion 31 starts the downward motion of the probe 12a by controlling the drive of the driving portion 12c (step S1).

Next, as shown in FIG. 5B, the control portion 31 determines whether or not the tip portion of the probe 12a reaches the first position P1 (step S2). In addition, when the control portion 31 determines that the tip portion of the probe 12a does not yet reach the first position P1 (determination of NO in step S2), the control portion 31 returns to step S1 and continues the downward motion of the probe 12a. Furthermore, when the control portion 31 determines that the tip portion of the probe 12a reaches the first position P1 (determination of YES in step S2), the control portion 31 stops the downward motion of the probe 12a by controlling the drive of the driving portion 12c. Thereby, the downward motion of the probe 12a is completed (step S3).

During the downward motion of the probe 12a, the control portion 31 detects the contact of the tip portion of the probe 12a with the liquid surface S, by the liquid surface detecting mechanism 32. Next, the control portion 31 sends the liquid surface detecting information and the first position P1 (hereinafter, referred to as "position information") obtained from the storage portion 34 to the calculation portion 35. Subsequently, the calculation portion 35 calculates a motion amount x of the probe 12a from the liquid surface S to the first position P1 based on the liquid surface detecting information and the position information. In addition, the calculation portion 35 sends the calculated motion amount x to the storage portion 34. The storage portion 34 receives the motion amount x, and stores and holds it.

Then, as shown in FIG. 6C, a given amount of the reagent L is sucked from the tip portion of the probe 12a (step S4) by activating a pump for the reagent (not shown) by the control portion 31. Thereby, the amount of the reagent L in the reagent container 24 is changed.

During the suction operation of the probe 12a, the control portion 31 causes the calculation portion 35 to start the calculation processing of the amount y of the upward motion of the probe 12a (step S5).

Here, one example of the calculation processing of the amount of the upward motion of the probe 12a will be explained by referring to FIG. 9.

Figure 9:
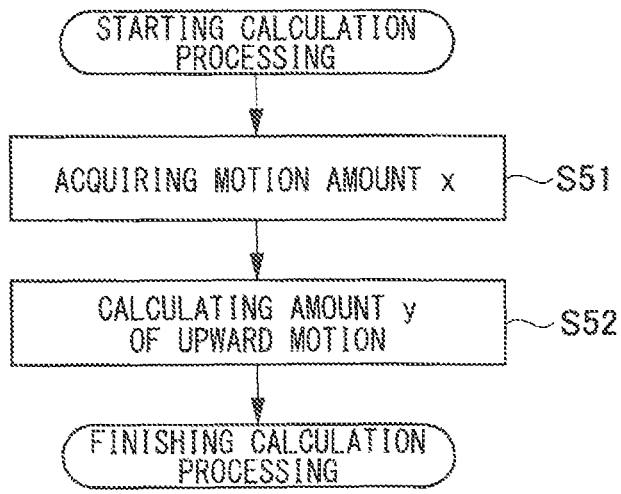
FIG. 9 is a flow chart showing one example of calculation processing of the amount of the upward motion of the probe.

FIG. 9 is a flow chart showing one example of calculation processing of the amount of the upward motion of the probe.

First, the calculation portion 35 acquires the motion amount x stored and held in the storage portion 34 (step S51). Next, the calculation portion 35 calculates the amount y of the upward motion based on the motion amount x (step S52).

Note that the amount y of the upward motion is an amount of the upward motion of the probe from the first position P1 to the second position P2 as shown in FIG. 6D. Furthermore, the amount y of the upward motion is calculated to be smaller than the motion amount x. The amount y of the upward motion here is calculated by considering the amount of the reagent L sucked by the suction operation of the probe 12a (step S4).

The second position P2 is a position near the liquid surface S of the reagent L and in the liquid of the reagent L, and is at least a position where the tip portion of the probe 12a is not separated from the reagent L. For example, in the second position P2, at least a part of the probe 12a may make contact with the liquid surface S of the reagent L in the case where the tip portion of the probe 12a has an inclined shape.

Then, the calculation portion 35 sends the calculated amount y of the upward motion to the storage portion 34. The storage portion 34 receives the amount y of the upward motion, and stores and holds it. Thereby, the control portion 31 completes the calculation processing of the amount y of the upward motion by the calculation portion 35.

Next, returning to FIG. 8, the control portion 31 causes the calculation portion 35 to start the calculation processing of the stop time t of the probe 12a (step S6).

Here, one example of the calculation processing of the stop time of the probe 12a will be explained by referring to FIG. 10.

Figure 10:
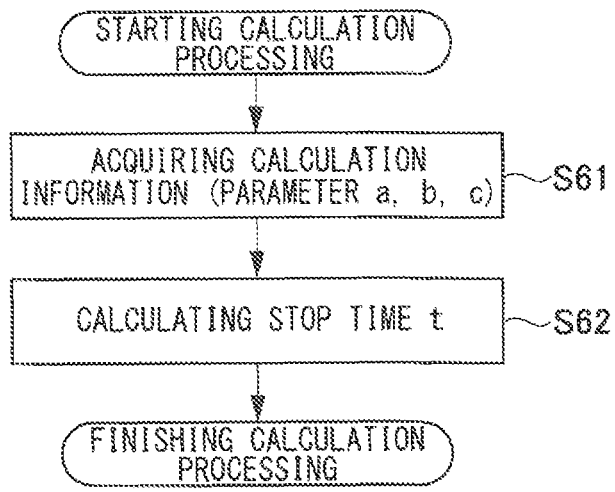
FIG. 10 is a flow chart showing one example of calculation processing of the period of stop time of the probe.

FIG. 10 is a flow chart showing one example of calculation processing of the stop time of the probe.

First, the calculation portion 35 acquires the calculation information stored and held in the storage portion 34 (step S61).

Examples of the calculation information include a viscosity, a surface tension of the reagent L, the first position P1, the amount y of the upward motion, a diameter of the probe 12a, quality of the probe 12a, and the like. In addition, there may be used a contact area (hereinafter, referred to as "first contact area") of the probe 12a with the reagent L at the time when the tip portion of the probe 12a stops at the first position P1.

Subsequently, the calculation portion 35 acquires shown in a parameter table of the following equation 1 and FIG. 4 from the storage portion 34. Then, the calculation portion 35 calculates the stop time t based on the equation 1 and the parameter table (step S62).

[Equation 1]

$$t \text{ [sec]} = 0.01 + (a+b+c)/100 \quad (1)$$

In the equation 1, a represents the value of the parameter a, b represents the value of the parameter b, and c represents the value of the parameter c.

Here, a calculation example of the stop time t of the probe 12a will be explained.

In this case, the "viscosity", the "surface tension" and the "first position" displayed on the display portion 33a shown in FIG. 3 are used as one example of the calculation information. For example, in the setting portion 33b displayed on the display portion 33a, the "viscosity" is set to "low", the "surface tension" is set to "low", and the "first position" is set to "shallow". Note that, in the parameter table shown in FIG. 4, the "viscosity" of the calculation information represents the parameter a, the "surface tension" represents the parameter b, and the "first position" represents the parameter c.

First, there are obtained the values of the parameters a, b, c which are substituted for the arithmetic equation (1) from the above described parameter table shown in FIG. 4. Here, as to the values of the parameters a, b, and c, the "parameter a (viscosity)" is "0", the "parameter b (surface tension)" is "2", the "parameter c (first position)" is "0" from the parameter table shown table shown in FIG. 4. Next, the calculation is performed by substituting the value of the parameters for the above equation (1). As a result, the stop time t is calculated as 0.03 [sec].

Here, as shown in the equation (1), the stop time t is prolonged depending on each value of the parameters as the standard unit of the stop time of 0.01 [sec]. In the parameter table shown in FIG. 4, the values of the "parameter a (viscosity)", the "parameter b (surface tension)", and the "parameter c (first position)" are determined based on the reasons explained below.

For example, a reagent L having a high viscosity gives a longer time to flow down into the reagent container 24 from the surface of the probe 12a than a reagent L having a low viscosity. Therefore, as to the "parameter a (viscosity)", the value of the parameter a is set to be large so that the higher the viscosity of the reagent L is, the longer the prolonged time becomes.

Furthermore, a reagent L having a low surface tension, due to its larger wettability, gives a longer time to flow down into the reagent container 24 from the surface of the probe 12a than a reagent L having a high surface tension. Accordingly, as to the "parameter b (surface tension)", the value of the parameter b is set to be large so that the lower the surface tension of the reagent L is, the longer the prolonged time becomes.

Moreover, the deeper the first position is, the larger the contact area (first contact area) of the probe 12a and the reagent L becomes, and thus the amount of the reagent L which follows the surface of the probe 12a becomes large. Therefore, the time to flow down into the reagent container 24 from the surface of the probe 12a is larger than the case where the first position is set shallow. Accordingly, as to the "parameter c (first position)", the value of the parameter c is set to be large so that the deeper the first position is, the longer the prolonged time becomes.

The values of the above equation (1) and the parameters shown in the parameter table are not limited thereto, and they may be appropriately set in accordance with the purpose and the intended use.

In addition, the calculation information is not limited to the "viscosity", "surface tension" and "first position". For example, other calculation information such as the amount y of the upward motion, the diameter of the probe 12a, the quality of the probe 12a, and the first contact area may be used as the calculation information. In addition, from the viewpoint of analytical accuracy, the first contact area or the first position P1 is preferably used as the calculation information.

Furthermore, the number of the parameters used in the equation (1) is not limited to three parameters of the "parameter a", the "parameter b", and the "parameter c". Namely, one or two parameters may be used, or three or more parameters may be used by adding other calculation information.

Then, the calculation portion 35 sends the calculated stop time t to the storage portion 34. In addition, the storage portion 34 receives the stop time t, and stores and holds it. Thereby, the control portion 31 completes the calculation processing of the stop time t by the calculation portion 35.

Next, returning to FIG. 8, the control portion 31 acquires the amount y of the upward motion and the stop time t from the storage portion 34. Then, the control portion 31 starts the upward motion of the probe 12a by control of the driving portion 12c (step S7).

Next, as shown in FIG. 6D, the control portion 31 determines whether or not the tip portion of the probe 12a reaches the second position P2 (step S8). In addition, in the case where the control portion 31 determines that the tip portion of the probe 12a does not yet reach the second position P2 (determination of NO in step S8), the control portion 31 returns to step S7 and continues the upward motion of the probe 12a. In the case where the control portion 31 determines that the tip portion of the probe 12a reaches the second position P2 (determination of YES in step S8), the control portion 31 stops the upward motion of the probe 12a by controlling the drive of the driving portion 12c (step S9).

Note that, when the tip portion of the probe 12*a* reaches the second position P2, a determination may be made as to whether or not the tip portion of the probe 12*a* is separated from the liquid surface S of the liquid by using the liquid surface detecting mechanism 32.

Next, the control portion 31 determines whether or not the stop time t elapses from the time when the upward motion of the probe 12*a* has been stopped (step S10). In the case where the control portion 31 determines that the stop time t does not elapse from the time when the stop of upward motion of the probe 12*a* has been started (determination of NO in step S10), the control portion 31 continues the determination processing. In the case where the control portion 31 determines that the stop time t elapses from the time when the stop of the upward motion of the probe 12*a* has been started (determination of YES in step S10), the control portion 31 proceeds to the next step S11. Note that the measurement of the time is carried out by, for example, utilizing a clock signal output by the CPU (not shown) which constitutes the control portion 31. Alternatively, a timer may be provided in the control portion 31.

Here, the change with the lapse of time in the liquid film of the reagent L which follows the tip portion of the probe 12*a* by the upward motion of the probe 12*a* will be explained by referring to FIGS. 7A and 7B.

FIG. 7A is an enlarged view of the tip portion of the probe shown in FIG. 6D.

As shown in FIG. 7A, the tip portion of the probe 12*a* stops at the second position P2, near the liquid surface S of the reagent L and in the liquid of the reagent L, based on the amount y of the upward motion. At this time, the reagent L follows the tip portion of the probe 12*a* by the upward motion of the probe 12*a*. The reagent L which follows the tip portion of the probe 12*a* adheres to the surface of the probe 12*a* as a liquid film L1. Then, the liquid film L1 adhering to the surface of the probe 12*a* is pulled to the reagent L in the reagent container 24 by the surface tension of the reagent L.

Furthermore, In the case where the stop time t elapses from the time when the upward motion of the probe 12*a* has been stopped, as shown in FIG. 7B, the liquid film L1 flow down into the reagent container 24 from the surface of the probe 12*a* by the surface tension of the reagent L gravity, and the like. Accordingly, the amount of the liquid film L1 can be reduced by stopping the tip portion of the probe 12*a* at the second position P2 and passing the stop time t.

In contrast, when separating the tip portion of the probe 12*a* from the liquid surface S, the liquid film L1 adhering to the surface of the probe 12*a* adheres to the tip portion of the probe 12*a* as a drop. Then, liquid droplets adhering to the tip portion of the probe 12*a* would not be pulled to the reagent L by the surface tension of the reagent L in the reagent container 24. Therefore, the liquid droplets adhering to the surface of the probe 12*a* is hard to flow down to the reagent container 24.

Accordingly, by the lifting and lowering motion of the probe 12*a* of the present exemplary embodiment, the amount of the liquid droplets adhering to the tip portion of the probe 12*a* can be reduced in comparison with the case where the tip portion of the probe 12*a* stops at the position separated from the liquid surface S.

Next, returning to FIG. 8, the control portion 31 starts the upward motion of the probe 12*a* by controlling the drive of the driving portion 12*c* (step S11). Then, as shown in FIG. 6E, the control portion 31 stops the upward motion of the probe 12*a* at a time when the tip portion of the probe 12*a* reaches the position which is separated from the reagent container 24 (refer to FIG. 6E). Thereby, the suction operation at the time of dispensing by the reagent dispensing mechanism 12 is completed.

Note that the suction operation by the reagent dispensing mechanism 12 has been explained as one example of the method for lifting and lowering the probe 12*a* according to the present exemplary embodiment, but the present invention is not limited thereto. Namely, the method for lifting and lowering the present exemplary embodiment is applicable to the dispensing operation of the specimen or the dispensing operation of the dilution liquid by the sample diluting dispensing mechanism 7, and also to the dispensing operation of the diluted specimen by the sampling dispensing mechanism 8. In addition, the method is applicable to the dispensing operation of the second reagent by the second reagent dispensing mechanism 13. Furthermore, the method is applicable to the dispensing operation and the cleaning operation.

In addition, the method for lifting and lowering motion of the present exemplary embodiment is applicable to the stirring operation of the dilution and stirring mechanism 9, the stirring operation of the first reaction stirring mechanism 14, or the stirring operation of the second reaction stirring mechanism 15.

The method for lifting and lowering motion of the probe 12*a* according to the present exemplary embodiment has been explained by referring the example of controlling downward motion of the probe 12*a* based on the predetermined first position P1, but method is not limited thereto, and the first position P1 may not be predetermined.

For example, in the downward motion of the probe 12*a*, the control portion 31 stops the probe 12*a* at the time when the liquid surface detecting mechanism 32 detects the contact of the tip portion of the probe 12*a* with the liquid surface S. Next, the control portion 31 measures a period of time until the probe 12*a* actually stops after making contact with the liquid surface S, to thereby acquire the information of the measurement time. Then, the control portion 31 sends the liquid surface detecting information and the information of the measurement time to the calculation portion 35. Subsequently, the calculation portion 35 calculates the motion amount x of the probe 12*a* from the liquid surface S to the stop position of the probe, based on the liquid surface detecting information and the information of the measurement time. Then, the first position P1 may be determined based on the calculated motion amount x. Furthermore, the amount y of the upward motion and the stop time t may be calculated based on the calculated motion amount x or the first position P1.

In addition, in the method for lifting and lowering the probe 12*a* of the present exemplary embodiment, the example of calculating the stop time t based on the calculation information by the calculation portion 35 has been explained, but the present invention is not limited thereto. For example, the control mechanism 30 may select the stop time t from a plurality of predetermined set values based on the calculated amount y of the upward motion. Note that the set values of the stop time t are previously calculated by the calculation portion 35, based on the information such as the type of the reagent L, the size and shape of the container.

In addition, in the method for lifting and lowering the probe 12*a* of the present exemplary embodiment, the motion speed of the probe 12*a* in the reagent dispensing mechanism 12 may be constant, or different by each motion such as downward motion or upward motion. For example, the control portion 31 may change the motion speed of the probe 12*a* before and after the stop of the upward motion of the probe 12a by control of the driving portion 12c. Furthermore, for example, it is possible to shorten the period of processing time by setting the motion speed of the probe 12a to a high speed.

Effects of the First Exemplary Embodiment

The above-described automated analyzer 1 of the present exemplary embodiment has the configuration in which there is performed the dispensing operation that dispenses the reagent L from the reagent container 24 to the reaction container 26 by the reagent dispensing mechanism 12 for dispensing the reagent L. Furthermore, the automated analyzer 1 has the configuration in which the control mechanism 30 for controlling the lifting and lowering motion of the probe 12a is provided. In addition, particularly, the control mechanism 30 stops the upward motion of the probe 12a for a given period of time at the second position P2 which is near the liquid surface S of the reagent L and in the liquid of the reagent L.

As explained in the above as to the change with the lapse of time of the liquid film L1 adhering to the surface of the probe 12a (refer to FIGS. 7A and 7B), according to the automated analyzer 1 of the present exemplary embodiment, it is possible to reduce the amount of the liquid film L1 adhering to the surface of the probe 12a. In addition, when the tip portion of the probe 12a is separated from the liquid surface S, it is possible to reduce the amount of the liquid droplets adhering to the tip portion of the probe 12a, and to suppress the variation in the absolute amount of the reagent L. Accordingly, the automated analyzer of the present exemplary embodiment can enhance the analytical accuracy.

Furthermore, it is preferable to set the amount y of the upward motion so that the contact area of the probe 12a with the reagent L at the time when the tip portion of the probe 12a stops at the second position P2 (hereinafter, referred to as "second contact area") is small. This is because the smaller the second contact area is, the smaller the friction force generated between the probe 12a and the reagent L can be made at the time when the upward motion of the probe 12a starts from the second position P2. Namely, the smaller the second contact area is, the smaller the amount of the reagent L which follows the surface of the probe 12a can be made. As a result, at the time when the tip portion of the probe 12a is separated from the liquid surface, the liquid droplets adhering to the tip portion of the probe 12a can be reduced.

Furthermore, according to the automated analyzer 1 of the present exemplary embodiment, the liquid droplets adhering to the tip portion of the probe 12a can be reduced regardless of the motion speed of the probe 12a. Therefore, for example, by setting the moving speed of the probe 12a to a high speed, the total processing time of the dispensing operation can be shortened.

Accordingly, the automated analyzer 1 of the present exemplary embodiment can rapidly measure a large number of components in addition to the above effects.

2. Second Exemplary Embodiment

2-1. Configuration of Automated Analyzer

Next, the configuration of the automated analyzer according to the second exemplary embodiment of the present invention will be explained by referring to FIG. 11.

Figure 11:
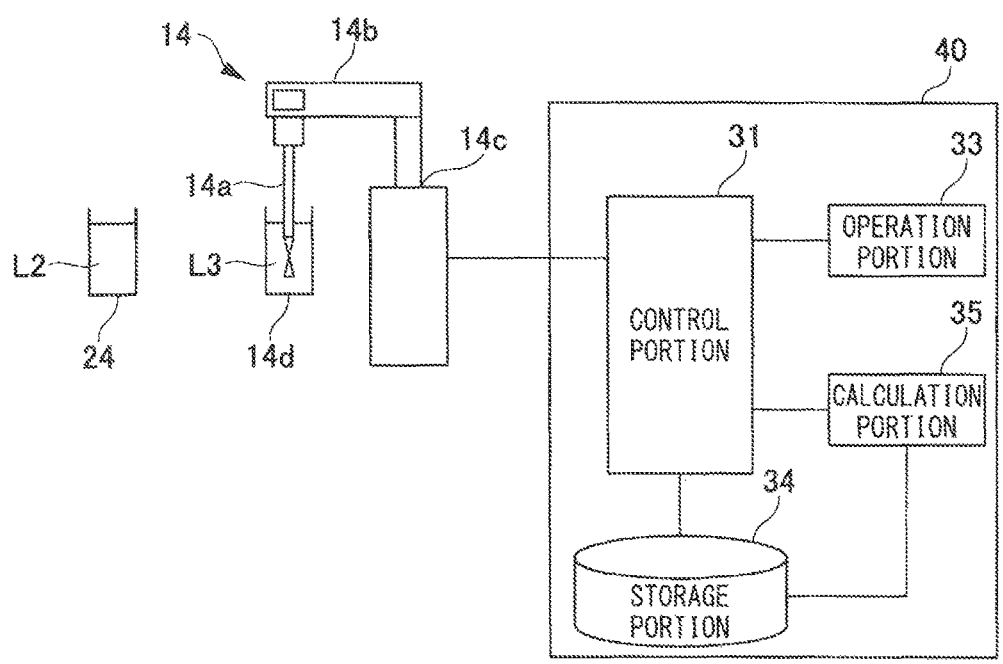
FIG. 11 is a block diagram showing the control mechanism, in the automated analyzer according to the second embodiment of the present invention.

FIG. 11 is a block diagram showing the control mechanism, in the automated analyzer according to the second exemplary embodiment of the present invention.

The different point of the automated analyzer according to the second exemplary embodiment from the automated analyzer 1 according to the first embodiment is to control the driving of the stirring mechanism. Accordingly, the configuration of the controlling of the stirring mechanism will be explained here. Furthermore, the case where the control mechanism 40 controls the first reaction stirring mechanism (hereinafter, referred to as "reaction stirring mechanism") 14 will be explained as one example.

Hereinafter, the same symbols are attached to constituent elements the same as the automated analyzer 1 according to the first embodiment, and the overlapped explanation is omitted, and only the different constituent elements will be explained. In addition, the "reagent" and the "specimen" are described together as "dispensing liquid", and the "first reaction stirring mechanism 14" is simply described as "reaction stirring mechanism 14".

[Reaction Stirring Mechanism 14]

As shown in FIG. 11, the reaction stirring mechanism 14 includes a stirring bar 14a which shows one example of the rod-like member, an arm 14b to which the stirring bar 14a is attached, a driving portion 14c which movably supports the arm 14b, and a cleaning bath 14d for cleaning the stirring bar 14a.

The reaction stirring mechanism 14 has a stirring driving portion (not shown) in the arm 14b to which the stirring bar 14a is attached. The stirring bar 14a is rotatably supported by the stirring driving portion around its axis. In addition, the stirring bar 14a stirs the dispensing liquid L2 injected into the reaction container 26, by rotation by the stirring driving portion. Note that the stirring movement by the stirring bar 14a is not limited thereto.

The stirring bar 14a is supported by the driving portion 14c via the arm 14b in the axial direction (for example, vertical direction) of the reaction turntable 6 (refer to FIG. 1) or the cleaning bath 14d in the movable manner. In addition, the stirring bar 14a is supported by the driving portion 14c via the arm 14b in the direction that bonds the reaction container 26 and the cleaning bath 14d (for example, horizontal direction) in the movable manner. Thus, the stirring bar 14a moves in the direction that bonds the reaction container 26 and the cleaning bath 14d, and reciprocates between the reaction container 26 and the cleaning bath 14d.

The cleaning bath 14d is formed in a shape of hollow container which is open at one face. The cleaning bath 14d has a supply port (not shown) through which a cleaning liquid L3 is supplied, and a discharge port through which the used cleaning liquid L3 is discharged. Then, the cleaning bath 14d cleans the stirring bar 14a by supplying the cleaning liquid L3 into the cleaning bath 14d.

The lifting and lowering motion of the stirring bar 14a of the reaction stirring mechanism 14 will be explained later.

[Control Mechanism 40]

As shown in FIG. 11, the control mechanism 40 includes the control portion 31, the operation portion 33, the storage portion 34 and the calculation portion 35. Namely, the different point of the control mechanism 40 from the control mechanism 30 of the automated analyzer 1 according to the first embodiment is that the control mechanism 40 does not include the liquid surface detecting mechanism 32. Furthermore, the control mechanism 40 is connected to the driving portion 14c of the reaction stirring mechanism 14. Then, the control mechanism 40 controls the lifting and lowering motion of the stirring bar 14a via the arm 14b by controlling the driving portion 14c of the reaction stirring mechanism 14.

Note that the control portion 31 is connected to the reaction stirring mechanism 14, the operation portion 33, the storage portion 34 and the calculation portion 35. In addition, the control portion 31 controls the reaction stirring mechanism 14, the operation portion 33, the storage portion 34 and the calculation portion 35.

Specifically, the control portion 31 controls a motion amount and motion speed in the lifting and lowering motion of the stirring bar 14a, the movement direction and movement speed in the movement motion, and the stirring operation and cleaning operation of the stirring bar 14a.

The storage portion 34 sends the information to and receives the information from the operation portion 33, the storage portion 34 and the calculation portion 35 of the control mechanism 40 under controlling by the control portion 31. In the storage portion 34, there are stored and held a program, information and a table of parameter for conducting the dispensing operation.

Examples of the program include a control program for controlling the operation of the reaction stirring mechanism 14, a calculation program for calculating the stop position (hereinafter, referred to as "second position") or the stop time of the stirring bar 14a, and the like. Examples of the information include the size (capacitance) of the reaction container 26, the shape of the reaction container 26, the type of the dispensing liquid L2 stored in the reaction container 26, the height of the liquid surface in the reaction container 26, the second position in the reaction container 26, the stop time in the reaction container 26, and the like. Furthermore, examples of the information include the size (capacitance) of the cleaning bath 14d, the shape of the cleaning bath 14d, the type of the cleaning liquid L3 stored in the cleaning bath 14d, the height of the liquid surface in the cleaning bath 14d, the second position in the cleaning bath 14d, the stop time in the cleaning bath 14d, and the like.

The calculation portion 35 calculates the height of the liquid surface, the second position and the stop time in the reaction container 26, before the lifting and lowering motion of the stirring bar 14a starts described below. In addition, the calculation portion 35 calculates the height of the liquid surface, the second position and the stop time in the cleaning bath 14d.

Since the other configuration is the same as of the automated analyzer 1 according to the first embodiment, an explanation thereof is omitted.

2-2. Method for Operating Stirring Mechanism in Automated Analyzer

Next, the method for operating the stirring mechanism in the automated analyzer will be explained by referring to FIG. 12.

Figure 12:
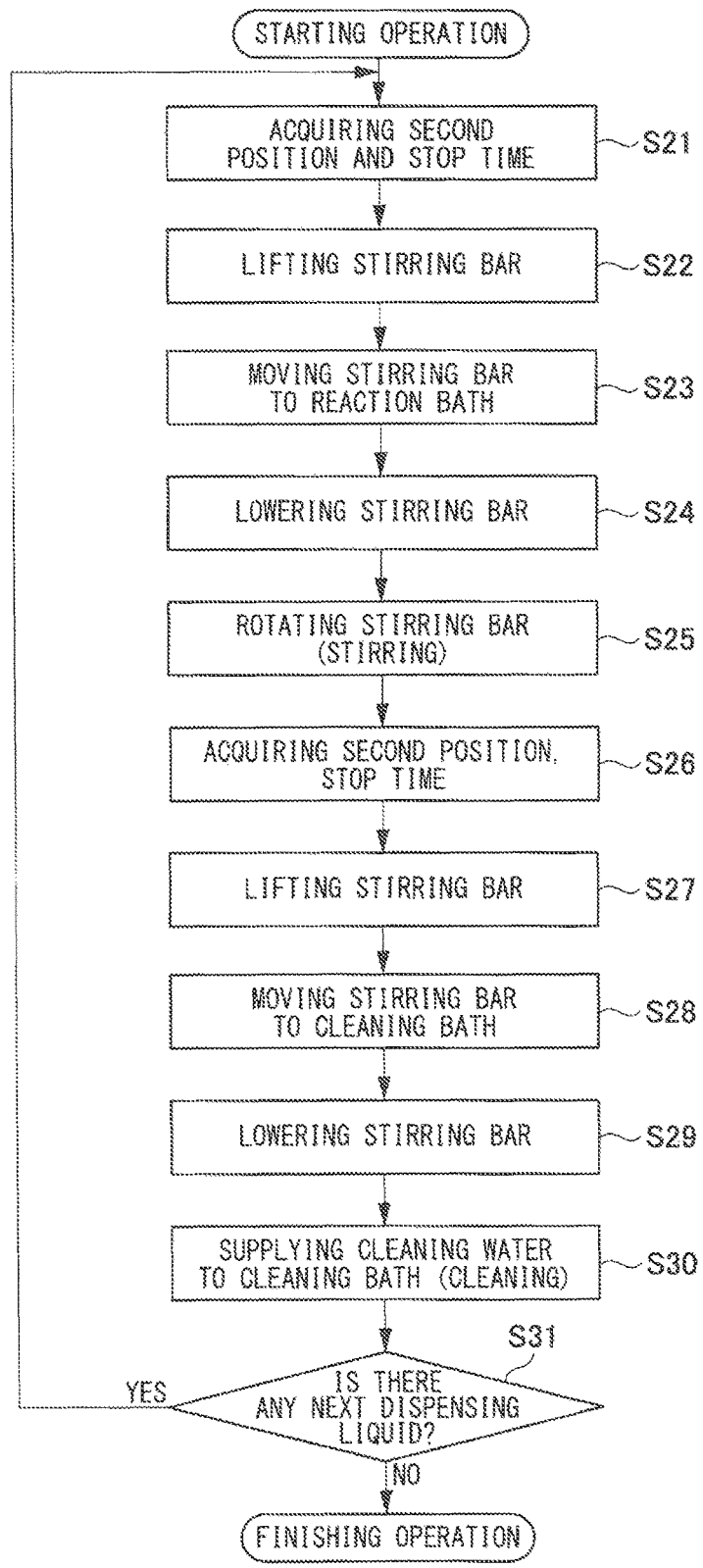
FIG. 12 is a flow chart showing the method for moving the stirring mechanism in the automated analyzer according to the second embodiment.

FIG. 12 is a flow chart showing the method for operating the stirring mechanism in the automated analyzer according to the second embodiment.

The different point of the operation method of the stirring mechanism in the automated analyzer according to the second embodiment, from the lifting and lowering motion of the probe 12a of the automated analyzer 1 according to the first embodiment, is that the height of the liquid surface is calculated without using the liquid surface detecting mechanism 32. Furthermore, the point that the second position is calculated based on the calculated height of the liquid surface is a different point from the lifting and lowering motion of the probe 12a of the automated analyzer 1 according to the first embodiment.

Therefore, here, there will be explained one example in which the height of the liquid surface is previously calculated from the information held in the storage portion 34, the second position is determined based on the height of the liquid surface, and then the operation method of the stirring mechanism starts. Furthermore, as to the operation method of the stirring mechanism of the second embodiment, the lifting and lowering motions at the time of the stirring and the cleaning by the reaction stirring mechanism 12 will be explained.

Note that, before the automated analysis procedures shown in FIG. 12, the user inputs, in the operation portion 33 shown in FIG. 3, the viscosity and surface tension of the dispensing liquid L2 to be stirred, and the first position in the reaction container 26 to be stirred. Moreover, in the same way, the user inputs the viscosity and surface tension of the cleaning liquid L3 to be supplied to the cleaning bath 14d and the first position in the cleaning bath 14d.

The calculation portion 35 previously calculates the height of the liquid surface in the reaction container 26, the second position in the reaction container 26, the stop time in the reaction container 26 and sends them to the storage portion 34. In addition, the calculation portion 35 previously calculates the height of the liquid surface in the cleaning bath 14d, the second position in the cleaning bath 14d, the stop time in the cleaning bath 14d and sends them to the storage portion 34. Then, the storage portion 34 receives the respective information of the calculated height of the liquid surface, the second position and the stop time, and stores and holds them.

Here, one example of calculation processing of the height of the liquid surface in the reaction container 26, the second position in the reaction container 26, and the stop time in the reaction container 26 as described above will be explained.

First, the calculation portion 35 acquires the amount of the dispensing liquid L2 stored in the reaction container 26 (hereinafter, referred to as "first information of liquid amount") and the capacity of the reaction container 26 (hereinafter, referred to as "first information of container capacity") from the storage portion 34. Next, the calculation portion 35 calculates the height of the liquid surface in the reaction container 26 based on the first information of liquid amount and the first information of container capacity. In addition, the calculation portion 35 calculates the second position in the reaction container 26 by subtracting a given value from the calculated height of the liquid surface. The given value is set as, for example, 1 mm. In this case, the second position is lower than the height of the liquid surface by 1 mm. Furthermore, the calculation portion 35 calculates the stop time in the reaction container 26 in the same way as in the calculation processing of the stop time t which is explained in the lifting and lowering motion of the automated analyzer 1 according to the exemplary first embodiment.

Note that the height of the liquid surface in the reaction container 26 is calculated based on the first information of the liquid amount and the first information of the container capacitance, but may be calculated based on the other information such as the type of the dispensing liquid L2, and the size and the shape of the reaction container 26. In addition, the given value to be subtracted from the height of the liquid surface is not limited to 1 mm, and may be used a value which is appropriately set in accordance with the purpose and use.

Furthermore, in the same way, the height of the liquid surface of the cleaning bath 14*d*, the second position in the cleaning bath 14*d*, and the stop time in the cleaning bath 14*d* are also calculated. First, the calculation portion 35 acquires the amount of the cleaning liquid L3 stored in the cleaning bath 14*d* (hereinafter, referred to as "second information of liquid amount") and the capacity of the cleaning bath 14*d* (hereinafter referred to as "second information of container capacity") from the storage portion 34. Next, the calculation portion 35 calculates the height of the liquid surface in the cleaning bath 14*d* based on the second information of liquid amount and the second information of container capacity. Then, the calculation portion 35 calculates the second position in the cleaning bath 14*d* by subtracting a given value from the calculated height of the liquid surface. In addition, the calculation portion 35 calculates the stop time in the cleaning bath 14*d* in the same way as in the calculation processing of the stop time t which is explained in the lifting and lowering motion of the automated analyzer 1 according to the first exemplary embodiment.

Note that the height of the liquid surface in the cleaning bath 14*d* is calculated based on the second information of the liquid amount and the second information of the container capacity, but may be calculated based on the other information such as the type of the cleaning liquid L3, and the size and the shape of the cleaning bath 14*d*.

In addition, the following procedures explained below are started, after completing cleaning of the stirring bar 14*a* by the cleaning bath 14*d* and at the time when the reaction container 26 to be stirred among a plurality of reaction container 26 stored in the reaction turntable 6 (refer to FIG. 1) reaches the stirring position. The reaction container 26 to be stirred moves to the dispensing position by rotationally driving the reaction turntable 6.

First, as shown in FIG. 12, the control portion 31 acquires the predetermined second position in the cleaning bath 14*d*, the stop time in the cleaning bath 14*d*, from the storage portion 34 (step S21). Then, the control portion 31 lifts the stirring bar 14*a* by controlling the driving portion 14*c* (step S22).

Note that the upward motion of the stirring bar 14*a* is conducted in the same way as in the upward motion in step S7 to step S11 which is explained in the method for lifting and lowering the automated analyzer 1 according to the first exemplary embodiment. Namely, in the upward motion of the stirring bar 14*a*, the tip portion of the stirring bar 14*a* is stopped at the second position P2 in the cleaning bath 14*d* based on the stop time in the cleaning bath 14*d* by the controlling of the control portion 31. Then, the control portion 31 completes the upward motion of the probe 12*b* at the time point when the tip portion of the stirring bar 14*a* reaches the position where the tip portion is separated from the cleaning bath 14*d*.

Next, the control portion 31 moves the stirring bar 14*a* to a given position above the opening in the reaction container 26, by control of the driving portion 14*c* (step S23).

Subsequently, the control portion 31 acquires the first position in the reaction container 26 from the storage portion 34. Note that the first position in the reaction container 26 is a position of the tip portion of the stirring bar 14*a* at the time when the downward motion of the stirring bar 14*a* is completed. Then, the control portion 31 lowers the stirring bar 14*a* to the first position in the reaction container 26 by controlling the driving portion 14*c* (step S24).

The downward motion of the stirring bar 14*a* is conducted in the same way as in step S1 to step S3 explained in the method for lifting and lowering the automated analyzer 1 according to the first exemplary embodiment, and thus its explanation is omitted.

Next, the control portion 31 stirs the dispensing liquid L2 by operating the stirring driving portion (not shown) (step S25). Thereby, the dispensing liquid L2 is stirred.

The control portion 31 acquires the second position in the reaction container 26 and the stop time in the reaction container 26, from the storage portion 34 (step S26). Then, the control portion 31 lifts the stirring bar 14*a* by controlling the driving portion 14*c* (step S27).

Note that the upward motion of the stirring bar 14*a* is conducted in the same way as in step S7 to step S11 explained in the method for lifting and lowering the automated analyzer 1 according to the first embodiment. Namely, in the upward motion of the stirring bar 14*a*, the tip portion of the stirring bar 14*a* is stopped at the second position P2 in the reaction container 26 based on the stop time in the reaction container 26 by the controlling of the control portion 31. Then, when the tip portion of the stirring bar 14*a* reaches the position where the tip portion is separated from the reaction container 26, the control portion 31 completes the upward motion of the probe 12*b*.

Next, the control portion 31 moves the probe 12*b* to a given position above the opening in the cleaning bath 14*d*, by control of the driving portion 14*c* (step S28).

Subsequently, the control portion 31 acquires the first position in the cleaning bath 14*d* from the storage portion 34. Note that the first position in the cleaning bath 14*d* is a position of the tip portion of the stirring bar 14*a* at the time when the downward motion of the stirring bar 14*a* is completed. Then, the control portion 31 lowers the stirring bar 14*a* to the first position in the cleaning bath 14*d*, by controlling the driving portion 14*c* (step S29).

Note that the downward motion of the stirring bar 14*a* is conducted in the same way as in step S1 to step S3 explained in the method for lifting and lowering the automated analyzer 1 according to the first embodiment, and thus its explanation is omitted.

Then, the stirring bar 14*a* is cleaned by supplying the cleaning liquid from a supply port (not shown) by the control portion 31 (step S30).

After that, the control portion 31 determines whether or not the measurement has been completed with respect to the predetermined number n of the dispensing liquid L2 (step S31). Then, in the case where the control portion 31 determines that the measurement has not yet been completed (determination of NO in step S31), the control portion 31 returns to step S21 and continues the lifting and lowering motion of step S21 to step S30. Furthermore, in the case where the control portion 31 determines that the measurement has been completed (determination of YES in step S31), the control portion 31 stops the operation of the reaction stirring mechanism 14. Thereby, the operation of the reaction stirring mechanism 14 is completed.

Note that the motion by the reaction stirring mechanism has been explained as the operation method of the stirring mechanism of the second exemplary embodiment, but the present invention is not limited thereto. Namely, the operation method of the stirring mechanism of the second exemplary embodiment is also applicable to the operation of the dilution and stirring mechanism 9, and the operation of the second reaction stirring mechanism 15.

Furthermore, in the operation method of the stirring mechanism of the second exemplary embodiment, the example of the lifting and lowering motion at the stirring and cleaning of the reaction stirring mechanism is explained, but the present invention is not limited thereto. Namely, only in the case of the lifting and lowering motion either at the time of the stirring or the cleaning, the upward motion may be conducted based on the predetermined second position and the stop time, in the same way as in step S7 to step S11 which is explained in the method for lifting and lowering the automated analyzer 1 according to the first exemplary embodiment.

Moreover, the lifting and lowering motion at the time of stirring and the cleaning of the reaction stirring mechanism of the second exemplary embodiment is applicable to the dispensing operation of the specimen and the dispensing operation of the dilution liquid by the sample diluting dispensing mechanism 7, or the dispensing operation of the diluted specimen by the sampling dispensing mechanism 8, and also applicable to the dispensing operation of the first reagent by the first reagent dispensing mechanism 12 and the dispensing operation of the second reagent by the second reagent dispensing mechanism 13. Furthermore, it is applicable to the dispensing operation and the cleaning operation.

Effects of Second Exemplary Embodiment

The above-described automated analyzer of the second embodiment has the configuration in which there are performed the stirring operation that stirs the dispensing liquid L2 in the reaction container 26 and the cleaning operation of the stirring bar 14*a*, by the reaction stirring mechanism 14 that stirs the dispensing liquid L2. Furthermore, the automated analyzer has the configuration in which the control mechanism 40 for controlling the lifting and lowering motion in the stirring movement by the stirring bar 14*a* and the cleaning operation of the stirring bar 14*a* is provided. In addition, particularly, the control mechanism 40 stops the upward motion of the stirring bar 14*a* for a given period of time at the second position which is near the liquid surface of the dispensing liquid L2 and in the liquid of the dispensing liquid L2. Moreover, the control mechanism 40 stops the upward motion of the stirring bar 14*a* for a given period of time at the second position which is near the liquid surface of the cleaning liquid L3 and in the liquid of the cleaning liquid L3. Accordingly, it is possible to obtain the same results as the first embodiment.

In addition, in the method for operating the stirring device of the second exemplary embodiment, the lifting and lowering motion in the stirring operation by the stirring bar 14*a* and the cleaning operation of the stirring bar 14*a* is conducted based on the predetermined second position and the stop time. Accordingly, since it is not necessary to perform calculation processing of the second position and the stop time for every lifting and lowering motion, the stirring treatment can be simplified.

The present invention is not limited to the above embodiments, and can be variously modified within the scope not deviating from the gist of the inventions described in Claims.

For example, as the automated analyzer of the present invention, there has been made an explanation of the example applied to a biochemical analyzer, but is not limited thereto, and the automated analyzer of the present invention can be applied to every automated analyzer which has a function of performing an operation of dispensing a liquid between two containers. Examples of such automated analyzers include an immunity analyzer, analyzers that analyze water quality, foods, and other various devices for analysis, and the like.

EXPLANATION OF SYMBOLS 1 automated analyzer
2 sample turntable
3 dilution turntable
4 first reagent turntable
5 second reagent turntable
6 reaction turntable
7 sample diluting dispensing mechanism
8 sampling dispensing mechanism
9 dilution and stirring mechanism
11 dilution cleaner
12 first reagent dispensing mechanism
13 second reagent dispensing mechanism
14 first reaction stirring mechanism (reaction stirring mechanism)
15 second reaction stirring mechanism
16 multi-wavelength photometer
17 thermostatic bath
18 reaction container cleaners
7*a*, 8*a*, 12*a*, 13*a* probe (rod-like member)
7*b*, 8*b*, 12*b*, 13*b*, 14*b* arm
7*c*, 8*c*, 12*c*, 13*c*, 14*a* stirring bar (rod-like member)
14*c* driving portion
14*d* cleaning bath
21 specimen container
22 dilution liquid container
23 dilution container
24 first reagent container (reagent container)
25 second reagent container
26 reaction container
30, 40 control mechanism
31 control portion
32 liquid surface detecting mechanism
33 operation portion
34 storage portion
35 operation portion
L reagent
L1 liquid film
L2 dispensing liquid
L3 cleaning liquid
P1 first position
P2 second position

What is claimed is:
1. An automated analyzer comprising:
a container for storing liquid,
a rod-like member having a tip portion for being inserted into and removed from the container where a liquid is stored,
a driving portion that lifts and lowers the rod-like member in a direction of the tip portion being inserted into and removed from the container, and
a control mechanism for controlling the motion of lifting and lowering the rod-like member with respect to the container,
wherein the control mechanism has a stored program that controls the driving portion so that the rod-like member is lifted after being lowered so that a tip portion of the rod-like member reaches a first position below the surface of the liquid, and at a time when the rod-like member reaches a second higher position but where the tip portion is not separated from the liquid, upward motion of the rod-like member is stopped for a stop time to permit the surface tension of the liquid to draw down liquid adhering to the surface of the rod-like member to reduce liquid film on the rod-like member, and then, after elapsing the given period of time, the rod-like member is lifted to a position where the tip portion is separated from the liquid.

2. The automated analyzer according to claim 1, wherein the control mechanism has a stored program that calculates the stop time of the rod-like member at the second position based on any one or more of the information of at least an amount of the upward motion of the rod-like member from the first position to the second position, a diameter of the rod-like member, quality of the rod-like member, a contact area of the rod-like member with the liquid at the first position, a viscosity of the liquid, or a surface tension of the liquid.

3. The automated analyzer according to claim 2, wherein the amount of the upward motion is calculated by the stored program so as to be smaller than a motion amount until the tip portion reaches the first position after making contact with the liquid.

4. The automated analyzer according to claim 1, wherein the control mechanism has a stored program that selects the stop time of the rod-like member at the second position, from among a plurality of specified values predetermined based on the information of the amount of the upward motion of the rod-like member from the first position to the second position.

5. The automated analyzer according to claim 1, comprising a surface detecting mechanism for determining whether or not the tip portion makes contact with or is separated from the liquid such that the determination is provided to the control mechanism.

6. The automated analyzer according to claim 5, wherein the control mechanism determines by the stored program the second position based on a position of a surface of the liquid stored in the container.

7. A method for lifting and lowering a rod-like member in an automated analyzer, comprising:
a first step of lowering a rod-like member, in a direction where a tip portion of the rod-like member makes contact with a liquid with respect to a container where the liquid is stored and so as to reach a first position in the liquid,
a second step of lifting the rod-like member after completing the first step, and stopping an upward motion of the rod-like member for a stop time to permit the surface tension of the liquid to draw down liquid adhering to the surface of the rod-like member to reduce liquid film on the rod-like member, at a time when at least the rod-like member reaches a second position where the tip portion is not separated from the liquid, and
a third step of lifting the rod-like member, after completing the second step, to a position where the tip portion is separated from the liquid.

* * * * *